United States Patent

Milde et al.

[19]

[11] Patent Number: 6,039,883
[45] Date of Patent: Mar. 21, 2000

[54] COMPOUND METHOD FOR DISINFECTION OF LIQUIDS

[75] Inventors: Helmut I Milde, Boxford; Sanborn F Philp, Pittsfield, both of Mass.

[73] Assignee: Ion Physics Corporation, Atkinson, N.H.

[21] Appl. No.: 08/983,533

[22] PCT Filed: Jul. 25, 1996

[86] PCT No.: PCT/US96/12174

§ 371 Date: Jan. 7, 1998

§ 102(e) Date: Jan. 7, 1998

[87] PCT Pub. No.: WO97/05067

PCT Pub. Date: Feb. 13, 1997

Related U.S. Application Data

[60] Provisional application No. 60/001,552, Jul. 27, 1995.

[51] Int. Cl.$^7$ ............................. C02F 1/461; A61L 2/02
[52] U.S. Cl. .......................... 210/748; 205/701; 205/742
[58] Field of Search ................................. 205/701, 742; 204/272; 210/748, 754, 764

[56] References Cited

U.S. PATENT DOCUMENTS

| 4,384,943 | 5/1983 | Stoner et al. | 204/149 |
| 4,492,618 | 1/1985 | Eder | 204/152 |
| 4,769,119 | 9/1988 | Grundler | 204/149 |
| 5,048,404 | 9/1991 | Bushnell et al. | 99/451 |
| 5,130,032 | 7/1992 | Sartori | 210/748 |
| 5,235,905 | 8/1993 | Bushnell et al. | 99/451 |
| 5,326,530 | 7/1994 | Bridges | 422/22 |

FOREIGN PATENT DOCUMENTS

| 22089 | 9/1972 | Germany | 204/272 |
| WO 83/02215 | 7/1983 | WIPO | 210/748 |

OTHER PUBLICATIONS

Dec.1990 IEEE Industry Applications Meeting 1712 90.
Copy of the International Search Report dated Jan. 8, 1997.

*Primary Examiner*—David A. Simmons
*Assistant Examiner*—Frank M. Lawrence
*Attorney, Agent, or Firm*—Nields, Lemack & Dingman

[57] ABSTRACT

Various chemical disinfectants, such as chlorine, have a broad capability for destroying or deactivating microbes, but can produce harmful disinfection by-products. They also result in residual contamination by the disinfecting chemical. The application of high potential gradients to a liquid medium containing microbes also has a powerful disinfecting action. The combination of chemical disinfectants with the electric process leads to a compound process of great effectiveness, whereby the electrical process acts with greater efficiency and the amounts of chemical disinfectant required are substantially reduced.

14 Claims, 1 Drawing Sheet

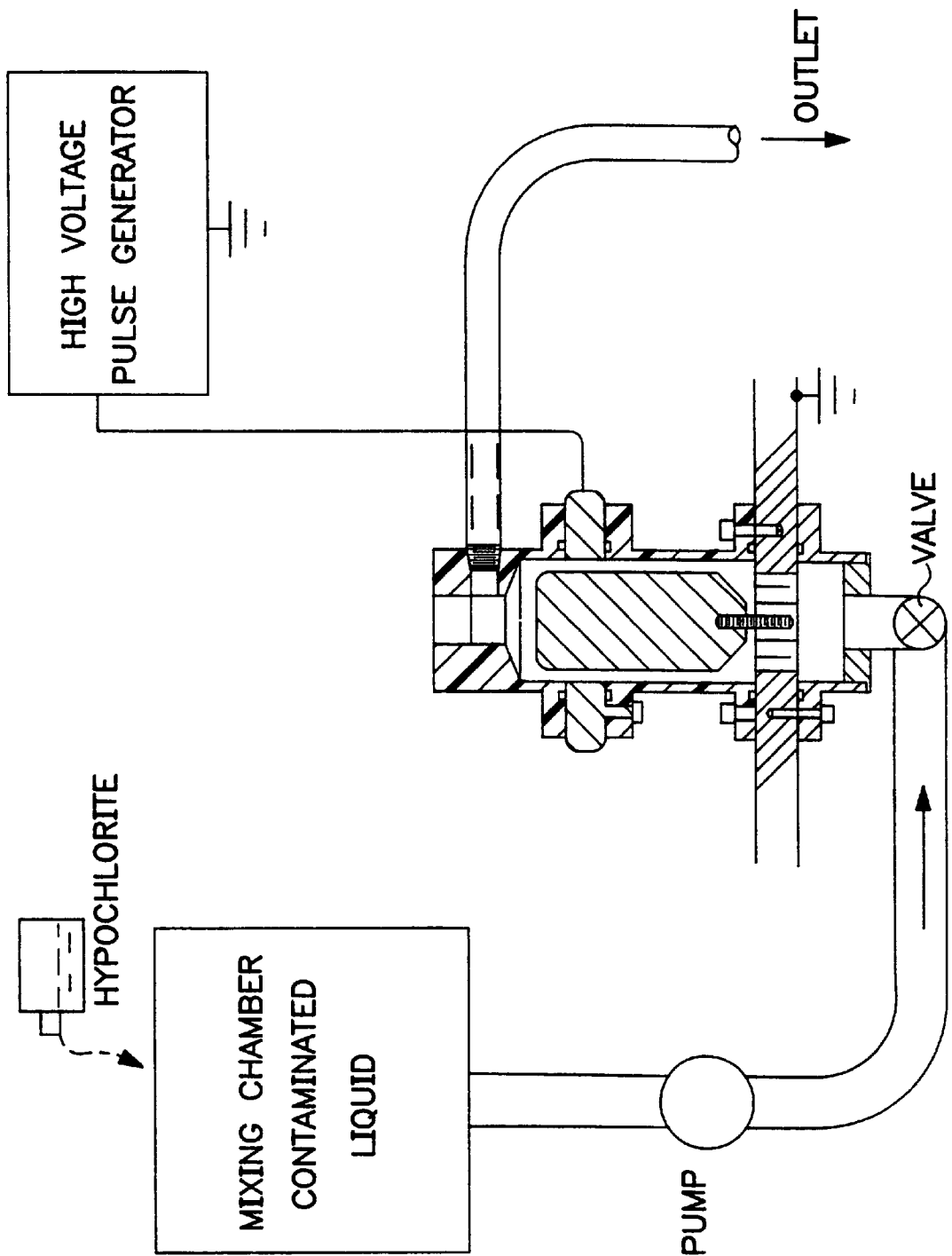

COMPOUND METHOD FOR DISINFECTION OF LIQUIDS

This application is a nonprovisional filing of U.S. provisional patent application Ser. No. 60/001,552 filed Jul. 27, 1995, now abandoned.

BACKGROUND OF THE INVENTION

1. Field of the Invention

This invention relates to the disinfection of liquids, especially those containing microbes, and combines the use of chemical disinfectants with the application of high potential gradients to a liquid medium containing microbes.

2. Description of the Related Art

High potential gradients applied to a medium containing microbes can destroy or deactivate the microbes. This has been known for at least fifty years. Sale and Hamilton were the first to publish definitive experimental data on this effect and to demonstrate that the effect was evidently due to the potential gradient per se, and not the result of heating or the passage of electric current. See, for example, A. J. H. Sale and W. A. Hamilton, *Effect of High Electric Fields on Microorganisms I. Killing of Bacteria and Yeasts*, Biochimica & Biophysica Acta 148, 781 (1967); W. A.Hamilton and A. J. H. Sale, *Effects of High Electric Fields on Microorganisms II. Mechanism of Action of the lethal Effect*, Biochimica & Biophysica Acta 148, 789 (1967); A. J. H. Sale and W. A. Hamilton, *Effect of High Electric Fields on Microorganisms III. Lysis of Erythrocytes and Protoplasts*, Biochimica & Biophysica Acta 163, 37 (1968). Subsequent microbiological studies by Benz and Läuger (see, for example, Roland Benz and P. Läuger, *Kinetic Analysis of Carrier-Mediated Ion Transport by the Charge-Pulse Techniaue*, Journ. Membrane Biol. 27, 171 (1976)), Zimmermann et al. (see, for example, Ulrich Zimmermann, J. Vienken & Günther Pilwat, *Development of drug Carrier Systems: Electrical Field-Induced Effects in Cell Membranes*, Bioelectrochem. & Bioenergetics 7, 553 (1980); Ulrich Zimmermann, Peter Scheurich, Günther Pilwat & Roland Benz, *Cells with Manipulated Functions: New Perspectives for Cell Biology, Medicine & Technology*, Angewandte Chemie 93, 332 (1981)), and Benz et al. (see, for example, Roland Benz, F. Beckers & Ulrich Zimmermann, *Reversible Electrical Breakdown of Lipid Bilayer Membranes: A Charge-Pulse Relaxation Study*, Journ. Membrane Biol. 48, 181 (1979); Roland Benz & Ulrich Zimmermann, *Pulse-Length Dependence of the Electrical Breakdown in Lipid Bilayer Membranes*, Biochimica & Biophysica Acta 597, 637 (1980)), showed that high potential gradients induce porosity in the membrane of a biological cell. Below a certain value of applied potential gradient—this critical value being of the order of 10 kV/cm—the induced porosity is reversible: That is, when the gradient is removed, the membrane regenerates its properties and the cell is not permanently affected. Whereas, for values of gradient above the critical value, porosity rapidly increases with increase in the applied gradient, and there is an increasing probability that the cell will be destroyed.

Various systems for applying high potential gradients to a medium containing microbes are disclosed in U.S. Pat. No. 5,048,404 to Bushnell et al. and in U.S. Pat. No. 5,235,905 to Bushnell et al.

SUMMARY OF THE INVENTION

As porosity of the membrane increases, there is an increase in the exchange of fluids between the interior of the cell and the medium which surrounds the cell. If a chemical disinfectant is present in the medium, this disinfectant will be carried into the cell with consequent adverse effect on cell viability. Potential gradients, by themselves, adversely affect a cell's viability. When the applied gradient exceeds the critical value and irreversible changes occur, both membrane porosity and the probability that the cell will be destroyed increase rapidly with increasing potential gradient. For these reasons, combining the high-potential gradient process with treatment by addition of small amounts of chemical disinfectant results in a process of high effectiveness.

Accordingly, in accordance with the invention, the liquid, contaminated with microbes, is contained within a processing chamber. Within this chamber are electrodes which themselves constitute part of the envelope of the contained volume of liquid to be processed. In this way, all fluid in the chamber—or all fluid passing through the chamber—is subjected to the high potential gradient, which is applied as a sequence of pulses. The applied potential gradients have an effect on the microbes which persists for a significant period of time after the application of the gradient has ceased—or after the microbe has passed out of the chamber where the gradients are applied. Even in the case of low gradients (say, of the order of 2000 V/cm), for which the membrane-related effects—such as porosity—are reversible, it has been shown (see hereinabove, Zimmermann, Vienken and Pilwat, 1980) that these effects persist for several minutes, at temperatures in the range 20° C. –30° C., and can persist for times of the order of an hour at 4° C. Consequently, there are several different modes for application of chemical disinfectant to a flowing stream of liquid which is to be disinfected by a combination of the chemical and high potential gradients: (1) The disinfectant can be added prior to (that is, up-stream from ) the electric field process. (2) It can be added simultaneously with the electric field process. (3) It can be added after (downstream from) the electric field process, provided that, in case (3), the locus for addition of the disinfectant must be a place in the fluid flow which the liquid would reach in less than (roughly) one minute after exposure to the potential gradient.

BRIEF DESCRIPTION OF THE DRAWINGS

The invention may best be understood from the following detailed description thereof, having reference to the accompanying drawings, in which:

FIG. 1 is a somewhat diagrammatic view of the process steps of the invention.

DESCRIPTION OF THE PREFERRED EMBODIMENT

Referring to the drawings, and first to FIG. 1 thereof, therein is shown an apparatus for carrying out the process of this invention and intended for the disinfection of a continuously flowing stream of liquid. This apparatus includes a means of mixing, which incorporates a valve and pipework, which permits a controllable stream of dilute disinfectant to flow continuously into the volume wherein mixing with the fluid occurs. The processing chamber contains an arrangement of electrodes such that the liquid to be processed is subjected to an electric field resulting from a potential difference maintained between various of these electrodes. The liquid enters first at an inlet pipe to the means of mixing, passes through this part of the apparatus, and then exits through a short pipe connecting into the electric field processing chamber. Baffles are provided in the mixing region (or the contents of the region may be continuously stirred) and the location of inlet and outlet are such that every element of input liquid spends a time in the mixing means which is approximately equal to the volume of this space divided by the volumetric rate of flow. From the mixing means, the liquid passes to the electric field processing chamber where high voltage pulses, applied at a certain rate across the electrodes, cause pulsed gradients to be induced in the liquid.

In one embodiment of the present invention, dielectric structures are introduced into the interelectrode gap or in the vicinity of the interelectrode gap in order to alter the configuration of the field.

The effectiveness of the subject invention is exemplified by the following experiments, in which chlorination and the pulsed gradient process are first applied separately and then combined into a single process. In each case, a liquid stream contaminated with coliform bacteria was passed through the apparatus. Samples were taken from the input stream and from the output stream for bacteriological analysis. Three different cases were studied:

(a) No chlorine was added to the disinfecting tank and the liquid stream was subjected only to pulsed gradients. The applied pulses produced a peak gradient of 40 kV/cm, and the pulse repetition rate was such, in relation to the velocity of flow, that every element of the liquid was subjected to approximately 20 pulses.

(b) A mixing tank was filled with several gallons of contaminated liquid and a dilute solution of hypochorite was introduced into the tank so that the added hypochlorite was in a proportion of 1.9 parts per million to the liquid volume in the tank. The residence time of the hypochlorite in the tank was 10 minutes. After this period, the liquid was dechlorinated with sodium bisulfite.

(c) The throughput liquid was subjected to both the electric field process described in (a) and the chlorination described in (b).

The results obtained from (a), (b) and (c) are summarized in the following Table:

Surviving Fraction of Microbes under Three Different Operating Conditions

|  | Total coliform bacteria | Fecal coliform bacteria |
| --- | --- | --- |
| (a) Pulsed field only | 0.0037 | 0.0048 |
| (b) Chlorine (Cl) only | 0.027 | 0.023 |
| (c) Pulsed field and Cl | less than 0.00013 | less than 0.0009 |

Having thus described the principles of the invention, together with illustrative embodiments thereof, it is to be understood that, although specific terms are employed, they are used in a generic and descriptive sense, and not for purposes of limitation, the scope of the invention being set forth in the following claims.

We claim:

1. A process for disinfection of liquids comprising the following steps:
   placing the contaminated liquid to be disinfected in an E-field processing chamber containing electrodes,
   applying at least one voltage pulse across said electrodes of sufficient magnitude and number to have a disinfecting action on said liquid, and
   adding to said liquid a disinfectant capable of increasing said disinfecting action produced by said voltage.

2. A process according to claim 1, wherein the contaminated liquid is placed in the processing chamber as a flowing stream of liquid.

3. A process according to claim 1, wherein the contaminated liquid is placed in the processing chamber as a given volume of liquid (a "batch") and not as a flowing stream of liquid; and to this batch of liquid said substance is added according to one or more of the following: (a) before, (b) during, or (c) after the E-field process.

4. A process according to claim 1, wherein the applied voltage and the geometry of the chamber and electrodes are such that a potential gradient of at least 1000 V/cm is produced within the liquid.

5. A process according to claim 1, wherein the pulses have a duration in time of one millisecond, or less, and are repeated at a rate of at least one pulse per second.

6. A process according to claim 1, wherein the potential gradient is produced by electrodes of shapes which result in a potential distribution which is uniform.

7. A process according to claim 1, wherein the potential gradient is produced by electrodes of shapes which result in a potential distribution which is approximately uniform—as in concentric cylindrical electrodes.

8. A process according to claim 1, wherein the potential gradient is produced by electrodes of shapes, which result in a potential distribution which is non-uniform.

9. A process according to claim 6, wherein dielectric structures are introduced into the interelectrode gap or in the vicinity of the interelectrode gap in order to alter the configuration of the field.

10. A process according to claim 7, wherein dielectric structures are introduced into the interelectrode gap or in the vicinity of the interelectrode gap in order to alter the configuration of the field.

11. A process according to claim 8, wherein dielectric structures are introduced into the interelectrode gap or in the vicinity of the interelectrode gap in order to alter the configuration of the field.

12. A process according to claim 2, wherein the said disinfectant is added in one or more of the following ways: (a) introduced into a chamber connected to, or a pipe leading to, the E-field p rocessing chamber and preceding this processing chamber in the flow path; (b) introduced into the E-field processing chamber itself; (c) introduced into a pipe or chamber which lies after the E-field processing chamber in the flow path.

13. A process according to claim 1, wherein said disinfectant is added to said liquid no later than one minute after said liquid leaves said chamber.

14. A process according to claim 1, wherein the applied voltage and the geometry of the chamber and electrodes are such that a potential gradient of at least 10,000 V/cm is produced within said liquid.

* * * * *